(12) United States Patent
Fennell

(10) Patent No.: US 7,948,369 B2
(45) Date of Patent: *May 24, 2011

(54) METHOD AND APPARATUS FOR PROVIDING DYNAMIC MULTI-STAGE SIGNAL AMPLIFICATION IN A MEDICAL DEVICE

(75) Inventor: Martin J. Fennell, Concord, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/849,004

(22) Filed: Aug. 2, 2010

(65) Prior Publication Data

US 2010/0295609 A1     Nov. 25, 2010

Related U.S. Application Data

(63) Continuation of application No. 12/102,836, filed on Apr. 14, 2008, now Pat. No. 7,768,387.

(60) Provisional application No. 60/911,866, filed on Apr. 14, 2007.

(51) Int. Cl.
    *G08B 29/00*      (2006.01)
(52) U.S. Cl. .................. 340/511; 422/68.1; 205/792
(58) Field of Classification Search .............. 340/511; 422/68.1; 330/85; 204/401; 205/792
See application file for complete search history.

(56) References Cited

U.S. PATENT DOCUMENTS

| | | | |
|---|---|---|---|
| 3,260,656 | A | 7/1966 | Ross, Jr. |
| 3,581,062 | A | 5/1971 | Aston |
| 3,926,760 | A | 12/1975 | Allen et al. |
| 3,949,388 | A | 4/1976 | Fuller |
| 4,036,749 | A | 7/1977 | Anderson |
| 4,055,175 | A | 10/1977 | Clemens et al. |
| 4,129,128 | A | 12/1978 | McFarlane |
| 4,245,634 | A | 1/1981 | Albisser et al. |
| 4,327,725 | A | 5/1982 | Cortese et al. |
| 4,344,438 | A | 8/1982 | Schultz |
| 4,349,728 | A | 9/1982 | Phillips et al. |
| 4,425,920 | A | 1/1984 | Bourland et al. |
| 4,478,976 | A | 10/1984 | Goertz et al. |
| 4,494,950 | A | 1/1985 | Fischell |
| 4,509,531 | A | 4/1985 | Ward |
| 4,527,240 | A | 7/1985 | Kvitash |
| 4,538,616 | A | 9/1985 | Rogoff |
| 4,619,793 | A | 10/1986 | Lee |
| 4,671,288 | A | 6/1987 | Gough |
| 4,703,756 | A | 11/1987 | Gough et al. |
| 4,731,726 | A | 3/1988 | Allen, III |

(Continued)

FOREIGN PATENT DOCUMENTS

DE     4401400     7/1995

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner* — John A Tweel, Jr.
(74) *Attorney, Agent, or Firm* — Jackson & Co., LLP

(57) ABSTRACT

Methods and apparatus for providing multi-stage signal amplification in a medical telemetry system are provided.

20 Claims, 4 Drawing Sheets

U.S. PATENT DOCUMENTS

| | | |
|---|---|---|
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,854,322 A | 8/1989 | Ash et al. |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,165,407 A | 11/1992 | Wilson et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,390,671 A | 2/1995 | Lord et al. |
| 5,391,250 A | 2/1995 | Cheney, II et al. |
| 5,408,999 A | 4/1995 | Singh et al. |
| 5,411,647 A | 5/1995 | Johnson et al. |
| 5,425,868 A | 6/1995 | Pedersen |
| 5,431,160 A | 7/1995 | Wilkins |
| 5,431,921 A | 7/1995 | Thombre |
| 5,438,271 A | 8/1995 | White et al. |
| 5,462,645 A | 10/1995 | Albery et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,609,575 A | 3/1997 | Larson et al. |
| 5,628,310 A | 5/1997 | Rao et al. |
| 5,653,239 A | 8/1997 | Pompei et al. |
| 5,665,222 A | 9/1997 | Heller et al. |
| 5,711,001 A | 1/1998 | Bussan et al. |
| 5,711,861 A | 1/1998 | Ward et al. |
| 5,772,586 A | 6/1998 | Heinonen et al. |
| 5,791,344 A | 8/1998 | Schulman et al. |
| 5,856,758 A | 1/1999 | Joffe et al. |
| 5,899,855 A | 5/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,049,727 A | 4/2000 | Crothall |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,478,736 B1 | 11/2002 | Mault |
| 6,484,046 B1 | 11/2002 | Say et al. |
| 6,514,718 B2 | 2/2003 | Heller et al. |
| 6,544,212 B2 | 4/2003 | Galley et al. |
| 6,551,494 B1 | 4/2003 | Heller et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,645,368 B1 | 11/2003 | Beaty et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |

| | | | | | | |
|---|---|---|---|---|---|---|
| 6,813,519 B2 | 11/2004 | Lebel et al. | | 2003/0100821 A1 | 5/2003 | Heller et al. |
| 6,862,465 B2 | 3/2005 | Shults et al. | | 2003/0125612 A1 | 7/2003 | Fox et al. |
| 6,873,268 B2 | 3/2005 | Lebel et al. | | 2003/0130616 A1 | 7/2003 | Steil et al. |
| 6,881,551 B2 | 4/2005 | Heller et al. | | 2003/0134347 A1 | 7/2003 | Heller et al. |
| 6,892,085 B2 | 5/2005 | McIvor et al. | | 2003/0168338 A1 | 9/2003 | Gao et al. |
| 6,895,263 B2 | 5/2005 | Shin et al. | | 2003/0176933 A1 | 9/2003 | Lebel et al. |
| 6,895,265 B2 | 5/2005 | Silver | | 2003/0187338 A1 | 10/2003 | Say et al. |
| 6,931,327 B2 | 8/2005 | Goode, Jr. et al. | | 2003/0199790 A1 | 10/2003 | Boecker et al. |
| 6,932,894 B2 | 8/2005 | Mao et al. | | 2003/0208113 A1 | 11/2003 | Mault et al. |
| 6,936,006 B2 | 8/2005 | Sabra | | 2003/0212317 A1 | 11/2003 | Kovatchev et al. |
| 6,950,708 B2 | 9/2005 | Bowman, IV et al. | | 2003/0212379 A1 | 11/2003 | Bylund et al. |
| 6,958,705 B2 | 10/2005 | Lebel et al. | | 2003/0216630 A1 | 11/2003 | Jersey-Willuhn et al. |
| 6,968,294 B2 | 11/2005 | Gutta et al. | | 2003/0217966 A1 | 11/2003 | Tapsak et al. |
| 6,971,274 B2 | 12/2005 | Olin | | 2004/0010207 A1 | 1/2004 | Flaherty et al. |
| 6,974,437 B2 | 12/2005 | Lebel et al. | | 2004/0011671 A1 | 1/2004 | Shults et al. |
| 6,990,366 B2 | 1/2006 | Say et al. | | 2004/0039298 A1 | 2/2004 | Abreu |
| 6,997,907 B2 | 2/2006 | Safabash et al. | | 2004/0040840 A1 | 3/2004 | Mao et al. |
| 6,998,247 B2 | 2/2006 | Monfre et al. | | 2004/0045879 A1 | 3/2004 | Shults et al. |
| 7,003,336 B2 | 2/2006 | Holker et al. | | 2004/0064068 A1 | 4/2004 | DeNuzzio et al. |
| 7,003,340 B2 | 2/2006 | Say et al. | | 2004/0106858 A1 | 6/2004 | Say et al. |
| 7,003,341 B2 | 2/2006 | Say et al. | | 2004/0122353 A1 | 6/2004 | Shahmirian et al. |
| 7,022,072 B2 | 4/2006 | Fox et al. | | 2004/0133164 A1 | 7/2004 | Funderburk et al. |
| 7,024,245 B2 | 4/2006 | Lebel et al. | | 2004/0138588 A1 | 7/2004 | Saikley et al. |
| 7,029,444 B2 | 4/2006 | Shin et al. | | 2004/0146909 A1 | 7/2004 | Duong et al. |
| 7,041,068 B2 | 5/2006 | Freeman et al. | | 2004/0152622 A1 | 8/2004 | Keith et al. |
| 7,052,483 B2 | 5/2006 | Wojcik | | 2004/0167801 A1 | 8/2004 | Say et al. |
| 7,056,302 B2 | 6/2006 | Douglas | | 2004/0171921 A1 | 9/2004 | Say et al. |
| 7,074,307 B2 | 7/2006 | Simpson et al. | | 2004/0176672 A1 | 9/2004 | Silver et al. |
| 7,081,195 B2 | 7/2006 | Simpson et al. | | 2004/0186362 A1 | 9/2004 | Brauker et al. |
| 7,098,803 B2 | 8/2006 | Mann et al. | | 2004/0186365 A1 | 9/2004 | Jin et al. |
| 7,108,778 B2 | 9/2006 | Simpson et al. | | 2004/0193025 A1 | 9/2004 | Steil et al. |
| 7,110,803 B2 | 9/2006 | Shults et al. | | 2004/0193090 A1 | 9/2004 | Lebel et al. |
| 7,113,821 B1 | 9/2006 | Sun et al. | | 2004/0197846 A1 | 10/2004 | Hockersmith et al. |
| 7,134,999 B2 | 11/2006 | Brauker et al. | | 2004/0199059 A1 | 10/2004 | Brauker et al. |
| 7,136,689 B2 | 11/2006 | Shults et al. | | 2004/0204687 A1 | 10/2004 | Mogensen et al. |
| 7,171,274 B2 | 1/2007 | Starkweather et al. | | 2004/0225338 A1 | 11/2004 | Lebel et al. |
| 7,190,988 B2 | 3/2007 | Say et al. | | 2004/0236200 A1 | 11/2004 | Say et al. |
| 7,192,450 B2 | 3/2007 | Brauker et al. | | 2004/0254433 A1 | 12/2004 | Bandis et al. |
| 7,198,606 B2 | 4/2007 | Boecker et al. | | 2004/0267300 A1 | 12/2004 | Mace |
| 7,226,978 B2 | 6/2007 | Tapsak et al. | | 2005/0004439 A1 | 1/2005 | Shin et al. |
| 7,267,665 B2 | 9/2007 | Steil et al. | | 2005/0004494 A1 | 1/2005 | Perez et al. |
| 7,276,029 B2 | 10/2007 | Goode, Jr. et al. | | 2005/0010269 A1 | 1/2005 | Lebel et al. |
| 7,299,082 B2 | 11/2007 | Feldman et al. | | 2005/0027177 A1 | 2/2005 | Shin et al. |
| 7,310,544 B2 | 12/2007 | Brister et al. | | 2005/0031689 A1 | 2/2005 | Shults et al. |
| 7,335,294 B2 | 2/2008 | Heller et al. | | 2005/0038332 A1 | 2/2005 | Saidara et al. |
| 7,354,420 B2 | 4/2008 | Steil et al. | | 2005/0043598 A1 | 2/2005 | Goode, Jr. et al. |
| 7,364,592 B2 | 4/2008 | Carr-Brendel et al. | | 2005/0090607 A1 | 4/2005 | Tapsak et al. |
| 7,366,556 B2 | 4/2008 | Brister et al. | | 2005/0096511 A1 | 5/2005 | Fox et al. |
| 7,379,765 B2 | 5/2008 | Petisce et al. | | 2005/0096512 A1 | 5/2005 | Fox et al. |
| 7,402,153 B2 | 7/2008 | Steil et al. | | 2005/0112169 A1 | 5/2005 | Brauker et al. |
| 7,424,318 B2 | 9/2008 | Brister et al. | | 2005/0113653 A1 | 5/2005 | Fox et al. |
| 7,460,898 B2 | 12/2008 | Brister et al. | | 2005/0114068 A1 | 5/2005 | Chey et al. |
| 7,467,003 B2 | 12/2008 | Brister et al. | | 2005/0121322 A1 | 6/2005 | Say et al. |
| 7,471,972 B2 | 12/2008 | Rhodes et al. | | 2005/0131346 A1 | 6/2005 | Douglas |
| 7,494,465 B2 | 2/2009 | Brister et al. | | 2005/0143635 A1 | 6/2005 | Kamath et al. |
| 7,497,827 B2 | 3/2009 | Brister et al. | | 2005/0176136 A1 | 8/2005 | Burd et al. |
| 7,519,408 B2 | 4/2009 | Rasdal et al. | | 2005/0177398 A1 | 8/2005 | Watanabe et al. |
| 7,547,281 B2 | 6/2009 | Hayes et al. | | 2005/0182306 A1 | 8/2005 | Sloan |
| 7,569,030 B2 | 8/2009 | Lebel et al. | | 2005/0187720 A1 | 8/2005 | Goode, Jr. et al. |
| 7,583,990 B2 | 9/2009 | Goode, Jr. et al. | | 2005/0192494 A1 | 9/2005 | Ginsberg |
| 7,591,801 B2 | 9/2009 | Brauker et al. | | 2005/0192557 A1 | 9/2005 | Brauker et al. |
| 7,599,726 B2 | 10/2009 | Goode, Jr. et al. | | 2005/0195930 A1 | 9/2005 | Spital et al. |
| 7,613,491 B2 | 11/2009 | Boock et al. | | 2005/0199494 A1 | 9/2005 | Say et al. |
| 7,615,007 B2 | 11/2009 | Shults et al. | | 2005/0203360 A1 | 9/2005 | Brauker et al. |
| 7,618,369 B2 | 11/2009 | Hayter et al. | | 2005/0239154 A1 | 10/2005 | Feldman et al. |
| 7,632,228 B2 | 12/2009 | Brauker et al. | | 2005/0241957 A1 | 11/2005 | Mao et al. |
| 7,768,387 B2 * | 8/2010 | Fennell ........................ 340/511 | | 2005/0245795 A1 | 11/2005 | Goode, Jr. et al. |
| 2002/0019022 A1 | 2/2002 | Dunn et al. | | 2005/0245799 A1 | 11/2005 | Brauker et al. |
| 2002/0042090 A1 | 4/2002 | Heller et al. | | 2005/0245839 A1 | 11/2005 | Stivoric et al. |
| 2002/0103499 A1 | 8/2002 | Perez et al. | | 2005/0245904 A1 | 11/2005 | Estes et al. |
| 2002/0106709 A1 | 8/2002 | Potts et al. | | 2005/0287620 A1 | 12/2005 | Heller et al. |
| 2002/0128594 A1 | 9/2002 | Das et al. | | 2006/0001538 A1 | 1/2006 | Kraft et al. |
| 2002/0161288 A1 | 10/2002 | Shin et al. | | 2006/0004270 A1 | 1/2006 | Bedard et al. |
| 2002/0169635 A1 | 11/2002 | Shillingburg | | 2006/0015020 A1 | 1/2006 | Neale et al. |
| 2003/0004403 A1 | 1/2003 | Drinan et al. | | 2006/0015024 A1 | 1/2006 | Brister et al. |
| 2003/0023317 A1 | 1/2003 | Brauker et al. | | 2006/0016700 A1 | 1/2006 | Brister et al. |
| 2003/0032874 A1 | 2/2003 | Rhodes et al. | | 2006/0019327 A1 | 1/2006 | Brister et al. |
| 2003/0042137 A1 | 3/2003 | Mao et al. | | 2006/0020186 A1 | 1/2006 | Brister et al. |
| 2003/0065308 A1 | 4/2003 | Lebel et al. | | 2006/0020187 A1 | 1/2006 | Brister et al. |

| | | | | | | |
|---|---|---|---|---|---|---|
| 2006/0020188 A1 | 1/2006 | Kamath et al. | | 2008/0194935 A1 | 8/2008 | Brister et al. |
| 2006/0020189 A1 | 1/2006 | Brister et al. | | 2008/0194936 A1 | 8/2008 | Goode et al. |
| 2006/0020190 A1 | 1/2006 | Kamath et al. | | 2008/0194937 A1 | 8/2008 | Goode et al. |
| 2006/0020191 A1 | 1/2006 | Brister et al. | | 2008/0194938 A1 | 8/2008 | Brister et al. |
| 2006/0020192 A1 | 1/2006 | Brister et al. | | 2008/0195232 A1 | 8/2008 | Carr-Brendel et al. |
| 2006/0029177 A1 | 2/2006 | Cranford, Jr. et al. | | 2008/0195967 A1 | 8/2008 | Goode et al. |
| 2006/0031094 A1 | 2/2006 | Cohen et al. | | 2008/0197024 A1 | 8/2008 | Simpson et al. |
| 2006/0036139 A1 | 2/2006 | Brister et al. | | 2008/0200788 A1 | 8/2008 | Brister et al. |
| 2006/0036140 A1 | 2/2006 | Brister et al. | | 2008/0200789 A1 | 8/2008 | Brister et al. |
| 2006/0036141 A1 | 2/2006 | Kamath et al. | | 2008/0200791 A1 | 8/2008 | Simpson et al. |
| 2006/0036142 A1 | 2/2006 | Brister et al. | | 2008/0208025 A1 | 8/2008 | Shults et al. |
| 2006/0036143 A1 | 2/2006 | Brister et al. | | 2008/0208113 A1 | 8/2008 | Damiano et al. |
| 2006/0036144 A1 | 2/2006 | Brister et al. | | 2008/0214915 A1 | 9/2008 | Brister et al. |
| 2006/0036145 A1 | 2/2006 | Brister et al. | | 2008/0214918 A1 | 9/2008 | Brister et al. |
| 2006/0155180 A1 | 7/2006 | Brister et al. | | 2008/0228051 A1 | 9/2008 | Shults et al. |
| 2006/0166629 A1 | 7/2006 | Reggiardo | | 2008/0228054 A1 | 9/2008 | Shults et al. |
| 2006/0173260 A1 | 8/2006 | Gaoni et al. | | 2008/0242961 A1 | 10/2008 | Brister et al. |
| 2006/0173406 A1 | 8/2006 | Hayes et al. | | 2008/0255434 A1 | 10/2008 | Hayter et al. |
| 2006/0173444 A1 | 8/2006 | Choy et al. | | 2008/0255437 A1 | 10/2008 | Hayter |
| 2006/0183985 A1 | 8/2006 | Brister et al. | | 2008/0255808 A1 | 10/2008 | Hayter |
| 2006/0189863 A1 | 8/2006 | Peyser et al. | | 2008/0256048 A1 | 10/2008 | Hayter |
| 2006/0222566 A1 | 10/2006 | Brauker et al. | | 2008/0262469 A1 | 10/2008 | Brister et al. |
| 2006/0224109 A1 | 10/2006 | Steil et al. | | 2008/0275313 A1 | 11/2008 | Brister et al. |
| 2006/0229512 A1 | 10/2006 | Petisce et al. | | 2008/0287761 A1 | 11/2008 | Hayter |
| 2006/0247508 A1 | 11/2006 | Fennell | | 2008/0287762 A1 | 11/2008 | Hayter |
| 2006/0272652 A1 | 12/2006 | Stocker et al. | | 2008/0287763 A1 | 11/2008 | Hayter |
| 2007/0016381 A1 | 1/2007 | Kamath et al. | | 2008/0287764 A1 | 11/2008 | Rasdal et al. |
| 2007/0027381 A1 | 2/2007 | Stafford | | 2008/0287765 A1 | 11/2008 | Rasdal et al. |
| 2007/0033074 A1 | 2/2007 | Nitzan et al. | | 2008/0287766 A1 | 11/2008 | Rasdal et al. |
| 2007/0060814 A1 | 3/2007 | Stafford | | 2008/0288180 A1 | 11/2008 | Hayter |
| 2007/0066873 A1 | 3/2007 | Kamath et al. | | 2008/0288204 A1 | 11/2008 | Hayter et al. |
| 2007/0071681 A1 | 3/2007 | Gadkar et al. | | 2008/0296155 A1 | 12/2008 | Shults et al. |
| 2007/0073129 A1 | 3/2007 | Shah et al. | | 2008/0306368 A1 | 12/2008 | Goode et al. |
| 2007/0078320 A1 | 4/2007 | Stafford | | 2008/0306434 A1 | 12/2008 | Dobbles et al. |
| 2007/0078321 A1 | 4/2007 | Mazza et al. | | 2008/0306435 A1 | 12/2008 | Kamath et al. |
| 2007/0078322 A1 | 4/2007 | Stafford | | 2008/0306444 A1 | 12/2008 | Brister et al. |
| 2007/0078323 A1 | 4/2007 | Reggiardo et al. | | 2008/0312841 A1 | 12/2008 | Hayter |
| 2007/0106135 A1 | 5/2007 | Sloan et al. | | 2008/0312842 A1 | 12/2008 | Hayter |
| 2007/0124002 A1 | 5/2007 | Estes et al. | | 2008/0312844 A1 | 12/2008 | Hayter et al. |
| 2007/0149875 A1 | 6/2007 | Ouyang et al. | | 2008/0312845 A1 | 12/2008 | Hayter et al. |
| 2007/0163880 A1 | 7/2007 | Woo et al. | | 2009/0005665 A1 | 1/2009 | Hayter et al. |
| 2007/0168224 A1 | 7/2007 | Letzt et al. | | 2009/0006034 A1 | 1/2009 | Hayter et al. |
| 2007/0173706 A1 | 7/2007 | Neinast et al. | | 2009/0012379 A1 | 1/2009 | Goode et al. |
| 2007/0173761 A1 | 7/2007 | Kanderian et al. | | 2009/0018424 A1 | 1/2009 | Kamath et al. |
| 2007/0179349 A1 | 8/2007 | Hoyme et al. | | 2009/0030294 A1 | 1/2009 | Petisce et al. |
| 2007/0179352 A1 | 8/2007 | Randlov et al. | | 2009/0033482 A1 | 2/2009 | Hayter et al. |
| 2007/0191701 A1 | 8/2007 | Feldman et al. | | 2009/0036747 A1 | 2/2009 | Hayter et al. |
| 2007/0203407 A1 | 8/2007 | Hoss et al. | | 2009/0036758 A1 | 2/2009 | Brauker et al. |
| 2007/0203966 A1 | 8/2007 | Brauker et al. | | 2009/0036760 A1 | 2/2009 | Hayter |
| 2007/0235331 A1 | 10/2007 | Simpson et al. | | 2009/0036763 A1 | 2/2009 | Brauker et al. |
| 2007/0249922 A1 | 10/2007 | Peyser et al. | | 2009/0043181 A1 | 2/2009 | Brauker et al. |
| 2008/0009692 A1 | 1/2008 | Stafford | | 2009/0043182 A1 | 2/2009 | Brauker et al. |
| 2008/0017522 A1 | 1/2008 | Heller et al. | | 2009/0043525 A1 | 2/2009 | Brauker et al. |
| 2008/0021666 A1 | 1/2008 | Goode, Jr. et al. | | 2009/0043541 A1 | 2/2009 | Brauker et al. |
| 2008/0029391 A1 | 2/2008 | Mao et al. | | 2009/0043542 A1 | 2/2009 | Brauker et al. |
| 2008/0033254 A1 | 2/2008 | Kamath et al. | | 2009/0045055 A1 | 2/2009 | Rhodes et al. |
| 2008/0039702 A1 | 2/2008 | Hayter et al. | | 2009/0055149 A1 | 2/2009 | Hayter et al. |
| 2008/0045824 A1 | 2/2008 | Tapsak et al. | | 2009/0062633 A1 | 3/2009 | Brauker et al. |
| 2008/0058625 A1 | 3/2008 | McGarraugh et al. | | 2009/0062635 A1 | 3/2009 | Brauker et al. |
| 2008/0064937 A1 | 3/2008 | McGarraugh et al. | | 2009/0062767 A1 | 3/2009 | VanAntwerp et al. |
| 2008/0071156 A1 | 3/2008 | Brister et al. | | 2009/0063402 A1 | 3/2009 | Hayter |
| 2008/0071157 A1 | 3/2008 | McGarraugh et al. | | 2009/0076356 A1 | 3/2009 | Simpson et al. |
| 2008/0071158 A1 | 3/2008 | McGarraugh et al. | | 2009/0076360 A1 | 3/2009 | Brister et al. |
| 2008/0081977 A1 | 4/2008 | Hayter et al. | | 2009/0076361 A1 | 3/2009 | Kamath et al. |
| 2008/0083617 A1 | 4/2008 | Simpson et al. | | 2009/0099436 A1 | 4/2009 | Brister et al. |
| 2008/0086042 A1 | 4/2008 | Brister et al. | | 2009/0105636 A1 | 4/2009 | Hayter et al. |
| 2008/0086044 A1 | 4/2008 | Brister et al. | | 2009/0124877 A1 | 5/2009 | Goode, Jr. et al. |
| 2008/0086273 A1 | 4/2008 | Shults et al. | | 2009/0124878 A1 | 5/2009 | Goode et al. |
| 2008/0097289 A1 | 4/2008 | Steil et al. | | 2009/0124879 A1 | 5/2009 | Brister et al. |
| 2008/0108942 A1 | 5/2008 | Brister et al. | | 2009/0124964 A1 | 5/2009 | Leach et al. |
| 2008/0154513 A1 | 6/2008 | Kovatchev et al. | | 2009/0131768 A1 | 5/2009 | Simpson et al. |
| 2008/0167543 A1 | 7/2008 | Say et al. | | 2009/0131769 A1 | 5/2009 | Leach et al. |
| 2008/0172205 A1 | 7/2008 | Breton et al. | | 2009/0131776 A1 | 5/2009 | Simpson et al. |
| 2008/0183060 A1 | 7/2008 | Steil et al. | | 2009/0131777 A1 | 5/2009 | Simpson et al. |
| 2008/0183061 A1 | 7/2008 | Goode et al. | | 2009/0137886 A1 | 5/2009 | Shariati et al. |
| 2008/0183399 A1 | 7/2008 | Goode et al. | | 2009/0137887 A1 | 5/2009 | Shariati et al. |
| 2008/0188731 A1 | 8/2008 | Brister et al. | | 2009/0143659 A1 | 6/2009 | Ying et al. |
| 2008/0188796 A1 | 8/2008 | Steil et al. | | 2009/0143660 A1 | 6/2009 | Brister et al. |
| 2008/0189051 A1 | 8/2008 | Goode et al. | | 2009/0156919 A1 | 6/2009 | Brister et al. |

| | | | |
|---|---|---|---|
| 2009/0156924 A1 | 6/2009 | Shariati et al. | |
| 2009/0163790 A1 | 6/2009 | Brister et al. | |
| 2009/0163791 A1 | 6/2009 | Brister et al. | |
| 2009/0164190 A1 | 6/2009 | Hayter | |
| 2009/0164239 A1 | 6/2009 | Hayter et al. | |
| 2009/0164251 A1 | 6/2009 | Hayter | |
| 2009/0178459 A1 | 7/2009 | Li et al. | |
| 2009/0182217 A1 | 7/2009 | Li et al. | |
| 2009/0192366 A1 | 7/2009 | Mensinger et al. | |
| 2009/0192380 A1 | 7/2009 | Shariati et al. | |
| 2009/0192722 A1 | 7/2009 | Shariati et al. | |
| 2009/0192724 A1 | 7/2009 | Brauker et al. | |
| 2009/0192745 A1 | 7/2009 | Kamath et al. | |
| 2009/0192751 A1 | 7/2009 | Kamath et al. | |
| 2009/0198118 A1 | 8/2009 | Hayter et al. | |
| 2009/0203981 A1 | 8/2009 | Brauker et al. | |
| 2009/0204341 A1 | 8/2009 | Brauker et al. | |
| 2009/0216103 A1 | 8/2009 | Brister et al. | |
| 2009/0240120 A1 | 9/2009 | Mensinger et al. | |
| 2009/0240128 A1 | 9/2009 | Mensinger et al. | |
| 2009/0240193 A1 | 9/2009 | Mensinger et al. | |
| 2009/0242399 A1 | 10/2009 | Kamath et al. | |
| 2009/0242425 A1 | 10/2009 | Kamath et al. | |
| 2009/0247855 A1 | 10/2009 | Boock et al. | |
| 2009/0247856 A1 | 10/2009 | Boock et al. | |
| 2009/0287073 A1 | 11/2009 | Boock et al. | |
| 2009/0287074 A1 | 11/2009 | Shults et al. | |
| 2009/0299155 A1 | 12/2009 | Yang et al. | |
| 2009/0299156 A1 | 12/2009 | Simpson et al. | |
| 2009/0299162 A1 | 12/2009 | Brauker et al. | |
| 2009/0299276 A1 | 12/2009 | Brauker et al. | |
| 2010/0057040 A1 | 3/2010 | Hayter | |
| 2010/0057041 A1 | 3/2010 | Hayter | |
| 2010/0057042 A1 | 3/2010 | Hayter | |
| 2010/0057044 A1 | 3/2010 | Hayter | |
| 2010/0057057 A1 | 3/2010 | Hayter et al. | |

FOREIGN PATENT DOCUMENTS

| | | | |
|---|---|---|---|
| EP | | 0098592 | 1/1984 |
| EP | | 0127958 | 12/1984 |
| EP | | 0320109 | 6/1989 |
| EP | | 0353328 | 2/1990 |
| EP | | 0390390 | 10/1990 |
| EP | | 0396788 | 11/1990 |
| EP | | 0286118 | 1/1995 |
| EP | | 1048264 | 11/2000 |
| WO | WO-96/25089 | | 8/1996 |
| WO | WO-96/35370 | | 11/1996 |
| WO | WO-98/35053 | | 8/1998 |
| WO | WO-99/56613 | | 11/1999 |
| WO | WO-00/49940 | | 8/2000 |
| WO | WO-00/59370 | | 10/2000 |
| WO | WO-00/78992 | | 12/2000 |
| WO | WO-01/52935 | | 7/2001 |
| WO | WO-01/54753 | | 8/2001 |
| WO | WO-02/16905 | | 2/2002 |
| WO | WO-02/058537 | | 8/2002 |
| WO | WO-03/076893 | | 9/2003 |
| WO | WO-03/082091 | | 10/2003 |
| WO | WO-03/085372 | | 10/2003 |
| WO | WO-2004/061420 | | 7/2004 |
| WO | WO-2005/041766 | | 5/2005 |
| WO | WO-2005/089103 | | 9/2005 |
| WO | WO-2006/024671 | | 3/2006 |
| WO | WO-2006/079114 | | 7/2006 |
| WO | WO-2006/118947 | | 11/2006 |
| WO | WO-2007/016399 | | 2/2007 |
| WO | WO-2007/027788 | | 3/2007 |
| WO | WO-2007/041069 | | 4/2007 |
| WO | WO-2007/041070 | | 4/2007 |
| WO | WO-2007/041248 | | 4/2007 |
| WO | WO-2007/056638 | | 5/2007 |
| WO | WO-2007/101223 | | 9/2007 |
| WO | WO-2007/120363 | | 10/2007 |
| WO | WO-2007/126444 | | 11/2007 |
| WO | WO-2007/053832 | | 12/2007 |
| WO | WO-2007/143225 | | 12/2007 |
| WO | WO-2008/021913 | | 2/2008 |
| WO | WO-2008/042760 | | 4/2008 |
| WO | WO-2008/128210 | | 10/2008 |
| WO | WO-2008/130896 | | 10/2008 |
| WO | WO-2008/130897 | | 10/2008 |
| WO | WO-2008/130898 | | 10/2008 |
| WO | WO-2008/143943 | | 11/2008 |
| WO | WO-2009/018058 | | 2/2009 |
| WO | WO-2009/086216 | | 7/2009 |
| WO | WO-2009/096992 | | 8/2009 |
| WO | WO-2009/097594 | | 8/2009 |

OTHER PUBLICATIONS

Bennion, N., et al., "Alternate Site Glucose Testing: A Crossover Design", *Diabetes Technology & Therapeutics*, vol. 4 No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56 No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain The Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectroscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp- 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

PCT Application No. PCT/US2008/060273, International Preliminary Report on Patentability and Written Opinion of the International Searching Authority mailed Oct. 29, 2009.

PCT Application No. PCT/US2008/060273, International Search Report and Written Opinion of the International Searching Authority mailed Oct. 1, 2008.

U.S. Appl. No. 12/102,836, Notice of Allowance mailed Jun. 18, 2010.

U.S. Appl. No. 12/102,836, Office Action mailed Mar. 11, 2010.

\* cited by examiner

US 7,948,369 B2

METHOD AND APPARATUS FOR PROVIDING DYNAMIC MULTI-STAGE SIGNAL AMPLIFICATION IN A MEDICAL DEVICE

RELATED APPLICATIONS

The present application is a continuation of U.S. application Ser. No. 12/102,836 filed Apr. 14, 2008, now U.S. Pat. No. 7,768,387, entitled "Method and Apparatus for Providing Dynamic Multi-Stage Amplification in a Medical Device", which claims the benefit of U.S. Provisional Application No. 60/911,866 filed Apr. 14, 2007, entitled "Method and Apparatus for Providing Dynamic Multi-Stage Amplification in a Medical Device", the disclosures of each of which are incorporated herein by reference for all purposes.

BACKGROUND

Analyte, e.g., glucose monitoring systems including continuous and discrete monitoring systems generally include a small, lightweight battery powered and microprocessor controlled system which is configured to detect signals proportional to the corresponding measured glucose levels using an electrometer, and RF signals to transmit the collected data. One aspect of certain analyte monitoring systems include a transcutaneous or subcutaneous analyte sensor configuration which is, for example, partially mounted on the skin of a subject whose analyte level is to be monitored. The sensor cell may use a two or three-electrode (work, reference and counter electrodes) configuration driven by a controlled potential (potentiostat) analog circuit connected through a contact system.

The analyte sensor may be configured so that a portion thereof is placed under the skin of the patient so as to detect the analyte levels of the patient, and another portion of segment of the analyte sensor that is in communication with the transmitter unit. The transmitter unit is configured to transmit the analyte levels detected by the sensor over a wireless communication link such as an RF (radio frequency) communication link to a receiver/monitor unit. The receiver/monitor unit performs data analysis, among others on the received analyte levels to generate information pertaining to the monitored analyte levels. To provide flexibility in analyte sensor manufacturing and/or design, among others, tolerance of a larger range of the analyte sensor sensitivities for processing by the transmitter unit is desirable.

In view of the foregoing, it would be desirable to have a method and apparatus for providing a dynamic multi-stage amplification of signals for use in medical telemetry systems such as, for example, analyte monitoring systems.

SUMMARY OF THE INVENTION

In one embodiment, an apparatus including a first amplifier having at least one input terminal and an output terminal, the at least one input terminal coupled to a signal source, the output terminal configured to provide a first output signal, a second amplifier having at least one input terminal and an output terminal, the at least one input terminal coupled to the output terminal of the first amplifier, the output terminal of the second amplifier configured to provide a second output signal, a processor operatively coupled to receive the first output signal and the second output signal, where the first output signal is a predetermined ratio of the second output signal, and further, where the first output signal and the second output signal are associated with a monitored analyte level of a user is disclosed.

These and other objects, features and advantages of the present invention will become more fully apparent from the following detailed description of the embodiments, the appended claims and the accompanying drawings.

DETAILED DESCRIPTION

As described in further detail below, in accordance with the various embodiments of the present invention, there is provided a method and apparatus for providing dynamic multi-stage signal amplification for use in a medical telemetry system. In particular, within the scope of the present invention, there are provided method and apparatus for a multi-stage signal amplifier configuration in the analog interface of the data transmitter unit in the data processing and management system.

Figure 1:
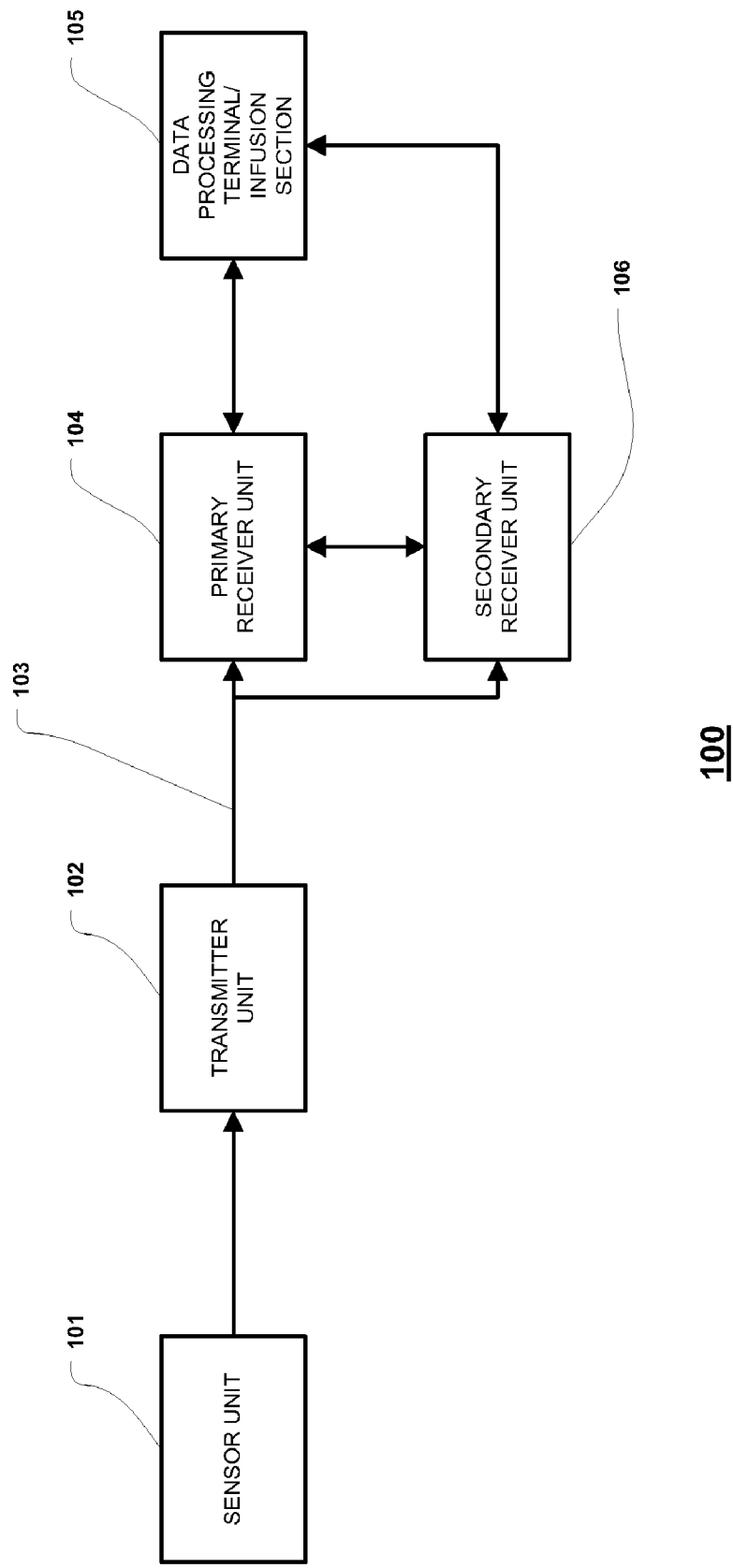
FIG. 1 illustrates a block diagram of a data monitoring and management system for practicing one or more embodiments of the present invention.

FIG. 1 illustrates a data monitoring and management system such as, for example, analyte (e.g., glucose) monitoring system 100 in accordance with one embodiment of the present invention. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The analyte monitoring system 100 includes a sensor 101, a transmitter unit 102 coupled to the sensor 101, and a primary receiver unit 104 which is configured to communicate with the transmitter unit 102 via a communication link 103. The primary receiver unit 104 may be further configured to transmit data to a data processing terminal 105 for evaluating the data received by the primary receiver unit 104. Moreover, the data processing terminal in one embodiment may be configured to receive data directly from the transmitter unit 102 via a communication link 103 which may optionally be configured for bi-directional communication.

Also shown in FIG. 1 is a secondary receiver unit 106 which is operatively coupled to the communication link and configured to receive data transmitted from the transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bi-directional wireless communication with each of the primary receiver unit 104 and the data processing terminal 105. As discussed in further detail below, in one embodiment of the present invention, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, for example. Alternatively, the secondary receiver unit 106 may be configured with the same or substantially similar functionality as the primary receiver unit 104, and may be configured to be used in conjunction with a docking cradle unit for placement by bedside, for night time monitoring, and/or bi-directional communication device.

Only one sensor 101, transmitter unit 102, communication link 103, and data processing terminal 105 are shown in the embodiment of the analyte monitoring system 100 illustrated in FIG. 1. However, it will be appreciated by one of ordinary skill in the art that the analyte monitoring system 100 may include one or more sensor 101, transmitter unit 102, communication link 103, and data processing terminal 105. Moreover, within the scope of the present invention, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present invention, the sensor 101 is physically positioned in or on the body of a user whose analyte level is being monitored. The sensor 101 may be configured to continuously sample the analyte level of the user and convert the sampled analyte level into a corresponding data signal for transmission by the transmitter unit 102. In one embodiment, the transmitter unit 102 is coupled to the sensor 101 so that both devices are positioned on the user's body, with at least a portion of the analyte sensor 101 positioned transcutaneously under the skin layer of the user. The transmitter unit 102 performs data processing such as filtering and encoding on data signals, each of which corresponds to a sampled analyte level of the user, for transmission to the primary receiver unit 104 via the communication link 103.

In one embodiment, the analyte monitoring system 100 is configured as a one-way RF communication path from the transmitter unit 102 to the primary receiver unit 104. In such embodiment, the transmitter unit 102 transmits the sampled data signals received from the sensor 101 without acknowledgement from the primary receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the primary receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the primary receiver unit 104.

Additionally, in one aspect, the primary receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the primary receiver unit 104 is a data processing section which is configured to process the data signals received from the transmitter unit 102 such as by performing data decoding, error detection and correction, data clock generation, and data bit recovery.

In operation, upon completing the power-on procedure, the primary receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the primary receiver unit 104 is configured to begin receiving from the transmitter unit 102 data signals corresponding to the user's detected analyte level. More specifically, the primary receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present invention, the data processing terminal 105 may include an infusion device such as an insulin infusion pump or the like, which may be configured to administer insulin to patients, and which may be configured to communicate with the receiver unit 104 for receiving, among others, the measured analyte level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the primary receiver unit 104 and the data processing terminal 105 may each be configured for bi-directional wireless communication such that each of the transmitter unit 102, the primary receiver unit 104 and the data processing terminal 105 may be configured to communicate (that is, transmit data to and receive data from) with each other via the wireless communication link 103. More specifically, the data processing terminal 105 may in one embodiment be configured to receive data directly from the transmitter unit 102 via the communication link 103, where the communication link 103, as described above, may be configured for bi-directional communication.

In this embodiment, the data processing terminal 105 which may include an insulin pump, may be configured to receive the analyte signals from the transmitter unit 102, and thus, incorporate the functions of the receiver 104 including data processing for managing the patient's insulin therapy and analyte monitoring. In one embodiment, the communication link 103 may include one or more of an RF communication protocol, an infrared communication protocol, a Bluetooth enabled communication protocol, an 802.11x wireless communication protocol, or an equivalent wireless communication protocol which would allow secure, wireless communication of several units (for example, per HIPPA requirements) while avoiding potential data collision and interference.

Figure 2:
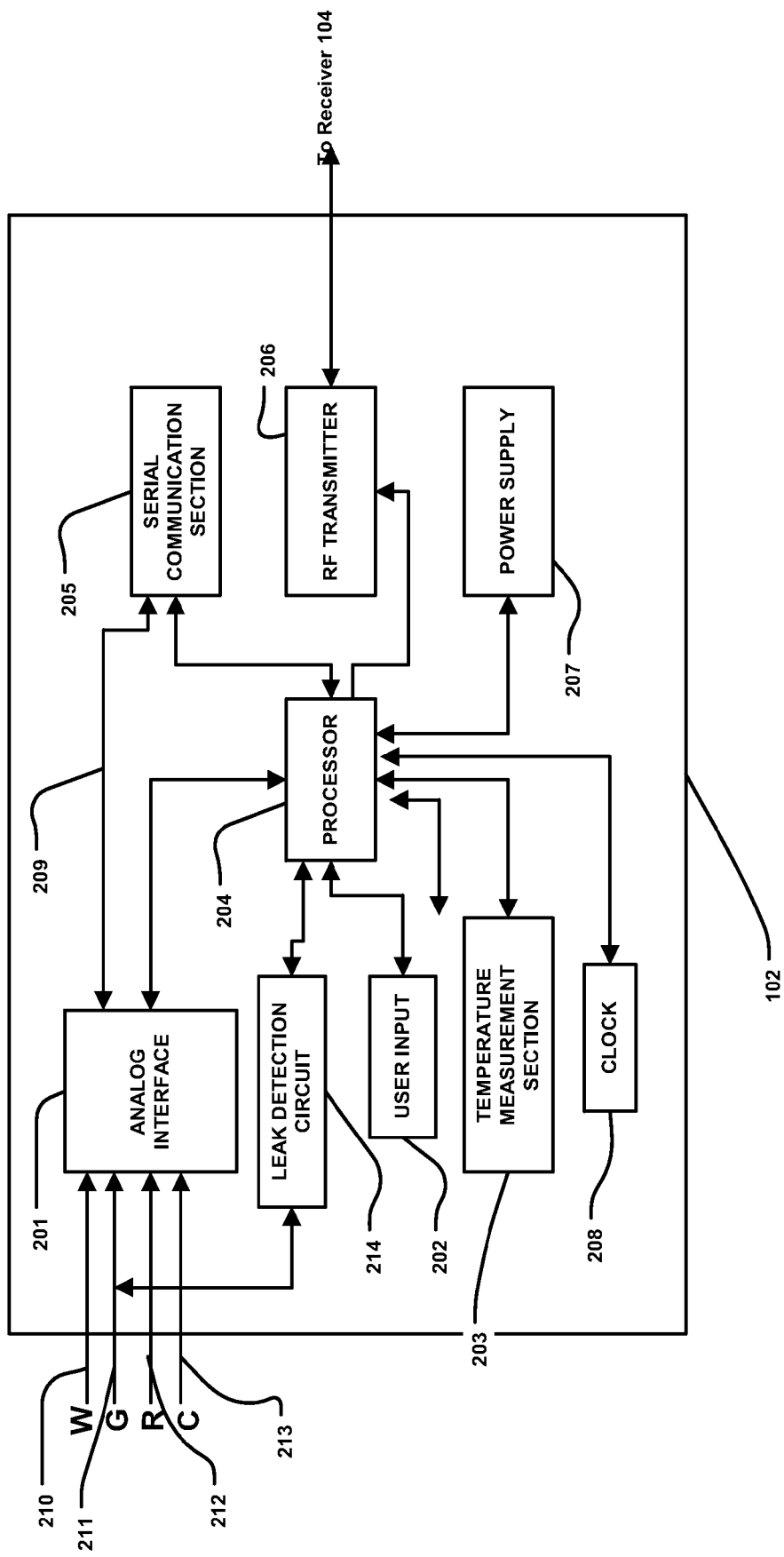
FIG. 2 is a block diagram of the transmitter unit of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter unit 102 in one embodiment includes an analog interface 201 configured to communicate with the sensor 101 (FIG. 1), a user input 202, and a temperature detection section 203, each of which is operatively coupled to a transmitter processor 204 such as a central processing unit (CPU). As can be seen from FIG. 2, there are provided four contacts, three of which are electrodes—work electrode (W) 210, guard contact (G) 211, reference electrode (R) 212, and counter electrode (C) 213, each operatively coupled to the analog interface 201 of the transmitter unit 102 for connection to the sensor unit 201 (FIG. 1). In one embodiment, each of the work electrode (W) 210, guard contact (G) 211, reference electrode (R) 212, and counter electrode (C) 213 may be made using a conductive material that is either printed or etched, for example, such as carbon which may be printed, or metal foil (e.g., gold) which may be etched. Moreover, in a further aspect, the electrode layers may be disposed in a stacked configuration where, each of the working electrode 210, the reference electrode 212 and the counter electrode 213 may be disposed on a substrate layer with one or more dielectric layers disposed therebetween such that at least a portion of each of the electrodes are positioned on top of one another in a stacked or layered configuration.

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

In one embodiment, a unidirectional input path is established from the sensor 101 (FIG. 1) and/or manufacturing and testing equipment to the analog interface 201 of the transmitter unit 102, while a unidirectional output is established from the output of the RF transmitter 206 of the transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the primary receiver unit 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor 101. The stored information may be retrieved and processed for transmission to the primary receiver unit 104 under the control of the transmitter processor 204. Furthermore, the power supply 207 may include a commercially available battery.

The transmitter unit 102 is also configured such that the power supply section 207 is capable of providing power to the transmitter for a minimum of about three months of continuous operation after having been stored for about eighteen months in a low-power (non-operating) mode. In one embodiment, this may be achieved by the transmitter processor 204 operating in low power modes in the non-operating state, for example, drawing no more than approximately 1 μA of current. Indeed, in one embodiment, the final step during the manufacturing process of the transmitter unit 102 may place the transmitter unit 102 in the lower power, non-operating state (i.e., post-manufacture sleep mode). In this manner, the shelf life of the transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present invention, the power supply unit 207 is configured to provide the necessary power to each of the components of the transmitter unit 102 shown in FIG. 2.

Referring back to FIG. 2, the power supply section 207 of the transmitter unit 102 in one embodiment may include a rechargeable battery unit that may be recharged by a separate power supply recharging unit (for example, provided in the receiver unit 104) so that the transmitter unit 102 may be powered for a longer period of usage time. Moreover, in one embodiment, the transmitter unit 102 may be configured without a battery in the power supply section 207, in which case the transmitter unit 102 may be configured to receive power from an external power supply source (for example, a battery) as discussed in further detail below.

Referring yet again to FIG. 2, the temperature detection section 203 of the transmitter unit 102 is configured to monitor the temperature of the skin near the sensor insertion site. The temperature reading is used to adjust the analyte readings obtained from the analog interface 201. The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the primary receiver unit 104.

Referring yet again to FIG. 2, also shown is a leak detection circuit 214 coupled to the guard electrode (G) 211 and the processor 204 in the transmitter unit 102 of the data monitoring and management system 100. The leak detection circuit 214 in accordance with one embodiment of the present invention may be configured to detect leakage current in the sensor 101 to determine whether the measured sensor data are corrupt or whether the measured data from the sensor 101 is accurate.

Additional detailed description of the continuous analyte monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to the Assignee of the present application, the disclosure of each of which are incorporated herein by reference for all purposes.

Figure 3:
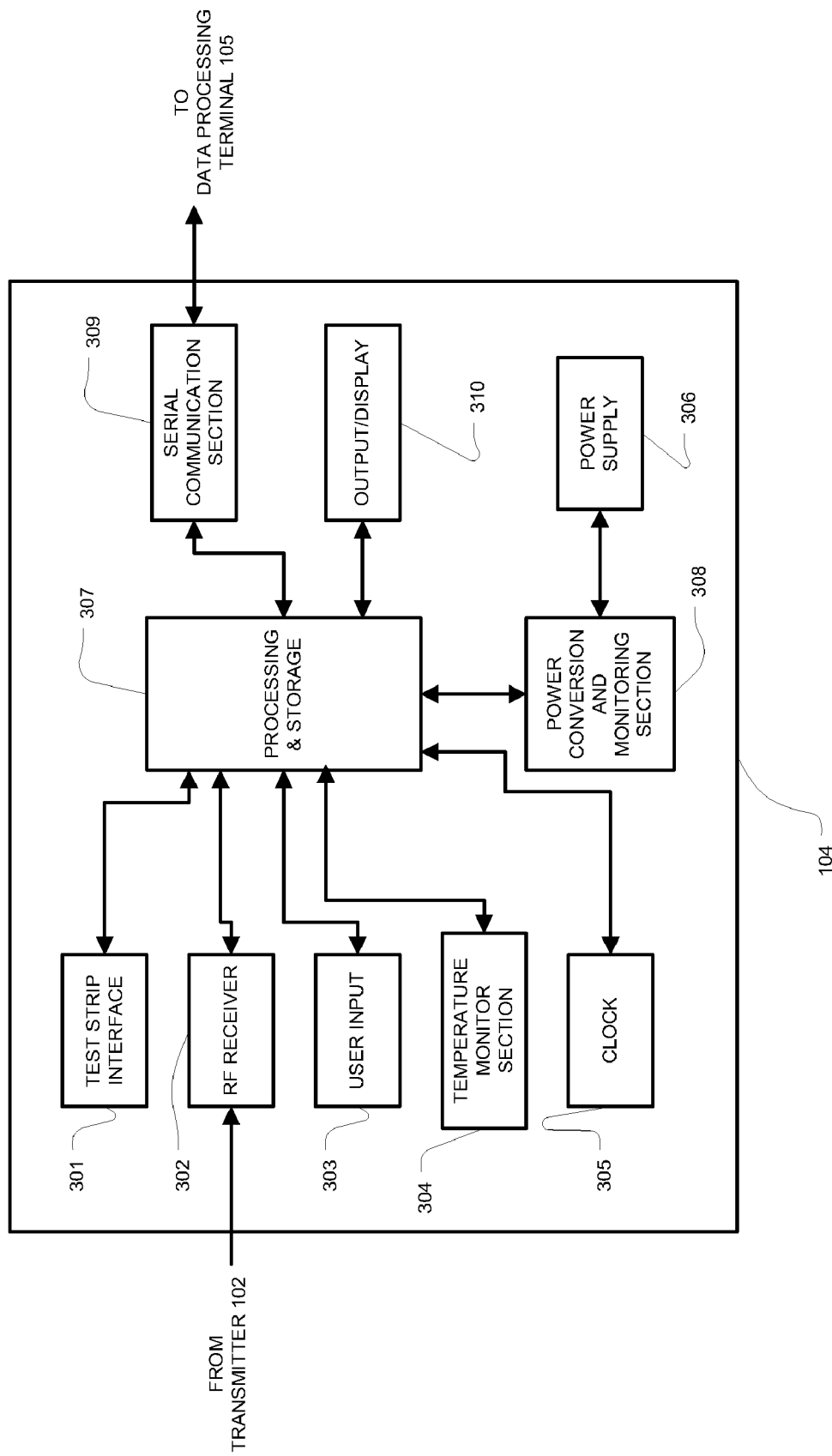
FIG. 3 is a block diagram of the receiver/monitor unit of the data monitoring and management system shown in FIG. 1 in accordance with one embodiment of the present invention.

FIG. 3 is a block diagram of the receiver/monitor unit of the data monitoring and management system shown in FIG. 1 in accordance with one embodiment of the present invention. Referring to FIG. 3, the primary receiver unit 104 includes a blood glucose test strip interface 301, an RF receiver 302, an input 303, a temperature detection section 304, and a clock 305, each of which is operatively coupled to a receiver processor 307. As can be further seen from the Figure, the primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the primary receiver unit 104. This manual testing of glucose can be used to calibrate sensor 101. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the primary receiver unit 104 is configured to allow the user to enter information into the primary receiver unit 104 as needed. In one aspect, the input 303 may include one or more keys of a keypad, a touch-sensitive screen, or a voice-activated input command unit. The temperature detection section 304 is configured to provide temperature information of the primary receiver unit 104 to the receiver processor 307, while the clock 305 provides, among others, real time information to the receiver processor 307.

Each of the various components of the primary receiver unit 104 shown in FIG. 3 is powered by the power supply 306 which, in one embodiment, includes a battery. Furthermore, the power conversion and monitoring section 308 is configured to monitor the power usage by the various components in the primary receiver unit 104 for effective power management and to alert the user, for example, in the event of power usage which renders the primary receiver unit 104 in sub-optimal operating conditions. An example of such sub-optimal operating condition may include, for example, operating the vibration output mode (as discussed below) for a period of time thus substantially draining the power supply 306 while the processor 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 104 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the primary receiver unit 104 also includes an electro-luminescent lamp configured to provide backlighting to the output 310 for output visual display in dark ambient surroundings.

Referring back to FIG. 3, the primary receiver unit 104 in one embodiment may also include a storage section such as a programmable, non-volatile memory device as part of the processor 307, or provided separately in the primary receiver unit 104, operatively coupled to the processor 307. The processor 307 is further configured to perform Manchester decoding as well as error detection and correction upon the encoded data signals received from the transmitter unit 102 via the communication link 103.

In a further embodiment, the one or more of the transmitter unit 102, the primary receiver unit 104, secondary receiver unit 105, or the data processing terminal/infusion section 105 may be configured to receive the blood glucose value wirelessly over a communication link from, for example, a glucose meter. In still a further embodiment, the user or patient manipulating or using the analyte monitoring system 100 (FIG. 1) may manually input the blood glucose value using, for example, a user interface (for example, a keyboard, keypad, and the like) incorporated in the one or more of the transmitter unit 102, the primary receiver unit 104, secondary receiver unit 105, or the data processing terminal/infusion section 105.

Figure 4:
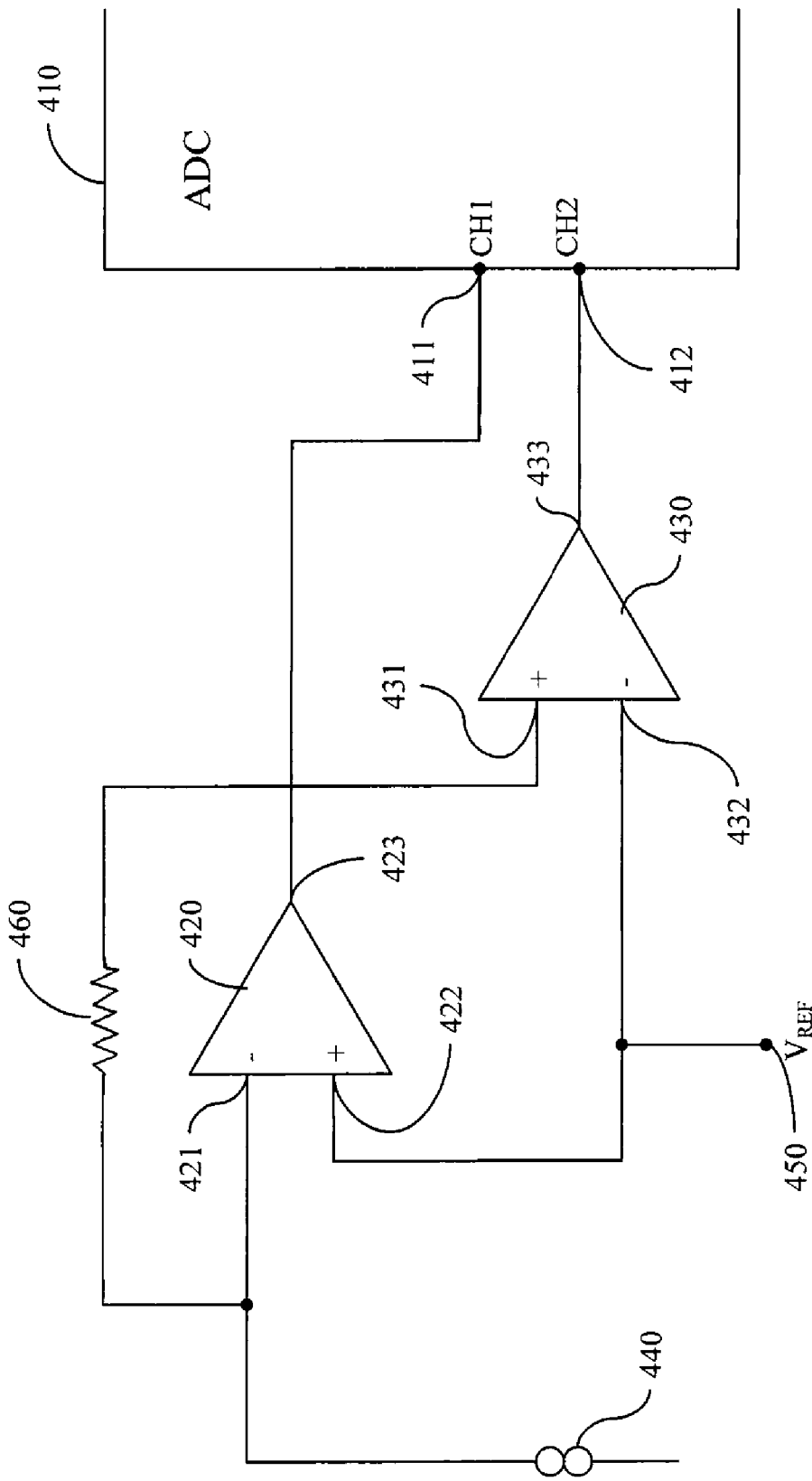
FIG. 4 is a schematic of the dynamic multi-stage signal amplification in the transmitter unit of the data monitoring and management system shown in FIG. 1 in accordance with one embodiment of the present invention.

FIG. 4 is a schematic of the dynamic multi-stage signal amplification in the transmitter unit of the data monitoring and management system shown in FIG. 1 in accordance with one embodiment of the present invention. Referring to FIG. 4, there is provided in one embodiment a transimpedance amplifier 420 whose output terminal 423 is coupled to a first input terminal 411 of the analog to digital converter (ADC) 410 in the analog interface 201 (FIG. 1) of the transmitter unit 102. Further shown in FIG. 4, the monitored analyte sensor signal from the sensor unit 101 is provided to an inverting input terminal 421 of the transimpedance amplifier 420. The sensor signal in FIG. 4 is shown as a signal source 440. Furthermore, a noninverting input terminal 422 of the transimpedance amplifier 420 is provided with a reference voltage signal from a reference signal source Vref 450. In one embodiment, the reference voltage signal may be approximately 1.012 volts. However, based upon the component tolerance, and design configuration, other suitable reference voltage signals may be used.

In one aspect, based on the input analyte sensor signal from the signal source 440 and the reference signal Vref 450, the transimpedance amplifier 420 may be in one embodiment configured to convert the received current signal representing the monitored or detected analyte level, and to convert the current signal to a corresponding voltage signal which is provided to the output terminal 423 of the transimpedance amplifier 420. Further, as shown in FIG. 4 the monitored analyte voltage signal from the output terminal 423 of the transimpedance amplifier 420 is provided to the first input terminal 411 (Channel 1) of the ADC 410.

Referring again to FIG. 4, a second amplifier 430 is provided in one embodiment whose noninverting input terminal 431 is coupled to the output terminal 423 of the transimpedance amplifier 420 to receive the output voltage signal corresponding to the monitored analyte level, while an inverting input terminal 432 of the second amplifier 430 is coupled in one embodiment to the reference signal Vref source 450. Moreover, output terminal 433 of the second amplifier is coupled in one embodiment to a second input terminal 412 (Channel 2) of the ADC 410. In operation, the second amplifier 430 may be configured to step up the output signal of the transimpedance amplifier 410 by a predetermined factor (for example, a factor of 2), and to provide the stepped up signal to the analog to digital converter (ADC) 410.

Referring back to FIG. 4, the analog to digital converter (ADC) 410 of the analog interface 201 (FIG. 2) of the transmitter unit 102 (FIG. 1) in one embodiment may be configured to detect signals at both the first and second input terminals or channels 411, 412, and based on one or more predetermined processing or routine, the voltage signal at one of the first or the second input terminals or channels 411, 412 is used by the ADC 410 for further processing as corresponding to the monitored analyte level from the sensor unit 101 (FIG. 1). That is, in one embodiment, depending upon the signal resolution corresponding to the analyte level monitored, the ADC 410 may be configured to select one of the output signals from the transimpedance amplifier 420 or the second amplifier 430 for further processing.

For example, when the signal received at the second input terminal 412 of the ADC 410 exceeds a predetermined threshold value, the input signal at the first input terminal 411 may be used. More specifically, in one embodiment, the ADC 410 may be configured to process the signals at the second input terminal 412 (Channel 2) since it has a higher resolution compared to the signal at the first input terminal 411 received from the transimpedance amplifier 420. When the signal received at the second input terminal 412 exceeds a predetermined threshold level (for example, based on the tolerance level of the analog to digital converter (ADC) 410), the voltage signal received at the first input terminal 411 from the transimpedance amplifier 420 may be used to convert to a corresponding digital signal representing the monitored analyte level detected by the sensor unit 101 (FIG. 1).

Referring back to FIG. 4, in one embodiment, the analog to digital converter (ADC) 410 may include a 12 bit A/D converter configured to support up to approximately 4,096 bits or ADC counts. In this case, in one embodiment, when the signal at the second input terminal 412 of the ADC 410 approaches approximately 4,000 bits or ADC counts, for example, the processor 204 (FIG. 2) of the transmitter unit 102 may be configured to switch from the second input terminal 412 to the first input terminal 411, to use the output signal from the transimpedance amplifier 420. In this manner, in one embodiment, the processor 204 of the transmitter unit 102 may be configured to monitor the signal levels at the two input terminals 411, 412 of the ADC 410, and when the signal level or ADC count associated with the output signal from the second amplifier 430 provided at the second input terminal 412 of the ADC 410 exceeds the predetermined threshold (for example, 4,000 bits or ADC count), the processor 204 may be configured to switch over to the output signal of the transimpedance amplifier 410 provided on the first input terminal 411 of the ADC 410 for further processing.

In the manner described above, the dynamic multi-stage amplifier configuration in one embodiment may be configured to support variations in the analyte sensor sensitivities due to, for example, manufacturing variations, among others, while maintaining an acceptable or desirable sensor signal resolution. For example, in one embodiment, high sensitivity sensors may be configured for use with the full scale or range (for example, up to approximately 150 nA corresponding to the supported approximately 500 mg/dL glucose level) associated with the transimpedance amplifier 420 output signal provided to the first input terminal (channel 1) 411 of the analog to digital converter (ADC) 410, while low sensitivity sensors may be associated with the second amplifier 430 output signal (for example, full scale current signal level of approximately 75 nA corresponding to the supported approximately 500 mg/dL glucose level) provided to the second input terminal (channel 2) 412 of the analog to digital converter (ADC) 410.

For example, as discussed above, in one embodiment, the processor 204 of the transmitter unit 102 may be configured to monitor the signals at the two input terminals 411, 412 of the ADC 410, and determine, that if the received signal level does not have sufficient resolution to convert to the desired resolution of the digital signal (for example, 12 bits for the ADC 410) corresponding to the monitored analyte level associated with the sensor unit 101, the processor 204 may be configured to dynamically toggle or switch from using the voltage signal received from one of the two input terminals 411, 412, to using the voltage signal from the other one of the two input terminals 411, 412 to provide a dynamic range of tolerance level for the sensor sensitivities.

Accordingly, an apparatus in one embodiment includes a first amplifier having at least one input terminal and an output terminal, the at least one input terminal coupled to a signal source, the output terminal configured to provide a first output signal, a second amplifier having at least one input terminal and an output terminal, the at least one input terminal coupled to the output terminal of the first amplifier, the output terminal of the second amplifier configured to provide a second output signal, a processor operatively coupled to receive the first output signal and the second output signal, where the first output signal is a predetermined ratio of the second output signal, and further, where the first output signal and the second output signal are associated with a monitored analyte level of a user.

In one aspect, the first amplifier may include a transimpedance amplifier.

The monitored analyte level may include glucose level.

Also, the at least one input terminal of the first amplifier may include an inverting input terminal, and, also may include a reference signal source coupled to a noninverting input terminal of the first amplifier.

In a further aspect, the second amplifier may include a gain of approximately two.

In still another aspect, the first output signal may be associated with a signal level from the signal source.

The apparatus may also include an analog to digital converter coupled to the output terminals of the first and second amplifiers, where the analog to digital (A/D) converter may include a 12 bit A/D converter.

The apparatus in another embodiment may include a processor operatively coupled to the A/D converter for processing the one or more signals received at the one or more first amplifier output terminal and the second amplifier output terminal.

Moreover, the processor may be configured to compare the one or more signals received at the one or more first amplifier output terminal and the second amplifier output terminal to a predetermined threshold value, which, in one embodiment may include approximately 4,000 bits (or analog to digital converter (ADC) counts)).

Still further, the processor may be configured to process a signal associated with one of the one or more signals received at the one or more first amplifier output terminal and the second amplifier output terminal when another signal associated with the other one of the one or more signals received at the one or more first amplifier output terminal and the second amplifier output terminal exceeds the predetermined threshold value.

A method in accordance with another embodiment includes receiving a first signal having a first signal resolution and associated with a monitored analyte level of a user, receiving a second signal having a second signal resolution and associated with the monitored analyte level of the user, comparing the received first signal to a predetermined threshold level, and processing one of the received first or the second signals based on the comparing step.

When the received first signal does not exceed the predetermined threshold level, further including processing the first signal. On the other hand, when the received first signal exceeds the predetermined threshold level, further including processing the second signal.

A data processing device in accordance with still another embodiment includes a multi stage amplifier unit configured to receive a signal and to generate a plurality of amplifier unit output signals each corresponding to a monitored analyte level of a patient, an analog to digital (A/D) conversion unit operatively coupled to the multi-stage amplifier unit configured to digitally convert the plurality of amplifier unit output signals, and a processor unit operatively coupled to the A/D conversion unit, the processor unit configured to process one of the plurality of digitally converted amplifier unit output signals.

The device in another aspect may include a data communication unit operatively coupled to the processor unit, and configured to transmit the digitally converted and processed amplifier unit output signal.

The data communication unit may include an RF transmitter for wireless data transmission to a remote device such as, for example, a data receiver unit, data processing terminal, an infusion device or the like configured for RF communication.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method, comprising:
coupling an input terminal of a first amplifier to a signal source, the first amplifier including an output terminal configured to provide a first output signal;
coupling an input terminal of a second amplifier to the output terminal of the first amplifier, the second amplifier including an output terminal configured to provide a second output signal, wherein the first output signal is a predetermined ratio of the second output signal, and the first output signal and the second output signal are associated with a monitored analyte level of a user;
operatively coupling an analog to digital (A/D) converter to the output terminals of the first and second amplifiers; and
providing a processor to receive the first output signal and the second output signal, the processor operatively coupled to the A/D converter and processing the one or more signals received at the one or more first amplifier output terminal and the second amplifier output terminal,
wherein providing the processor to receive the first output signal and the second output signal includes comparing the one or more signals received at the one or more first amplifier output terminal and the second amplifier output terminal to a predetermined threshold value, and processing a signal associated with one of the one or more signals received at the first amplifier output terminal and the second amplifier output terminal when another signal associated with the other one of the signals received at the first amplifier output terminal and the second amplifier output terminal exceeds the predetermined threshold value.

2. The method of claim 1 wherein the first amplifier includes a transimpedance amplifier.

3. The method of claim 1 wherein the monitored analyte level includes a glucose level.

4. The method of claim 1 wherein the input terminal of the first amplifier includes an inverting input terminal.

5. The method of claim 4 further including coupling a reference signal source to a noninverting input terminal of the first amplifier.

6. The method of claim 1 wherein the second amplifier includes a gain of approximately two.

7. The method of claim 1 wherein the first output signal is associated with a signal level from the signal source.

8. The method of claim 1 wherein the analog to digital (A/D) converter is a 12 bit A/D converter.

9. The method of claim 1 wherein the predetermined threshold value includes approximately 4,000 bits.

10. The method of claim 1 further including configuring the signal source to receive an analyte sensor signal.

11. The method of claim 10 wherein the analyte sensor signal corresponds to a monitored analyte level.

12. The method of claim 10 wherein the analyte sensor signal includes a glucose sensor signal.

13. The method of claim 1 further including operatively coupling the signal source to an analyte sensor.

14. The method of claim 13 wherein the analyte sensor includes a glucose sensor.

15. The method of claim 1 further including operatively coupling a data communication unit to the processor to communicate data associated with one or more signals at the signal source.

16. The method of claim 15 further including configuring the data communication unit to wirelessly communicate the data.

17. The method of claim 15 further including configuring the data communication unit to communicate data using a radio frequency communication protocol.

18. The method of claim 15 further including configuring the data communication unit to communicate data to a remote location.

19. The method of claim 18 further including displaying the data communicated to the remote location.

20. The method of claim 1 further including configuring the processor to toggle between the signal at the first amplifier output terminal and the signal at the second amplifier output terminal.

* * * * *